United States Patent [19]

Moest et al.

[11] Patent Number: 5,453,280
[45] Date of Patent: Sep. 26, 1995

[54] PRODUCTION OF PELLETS COMPOSED OF AN EPHEDRINE DERIVATIVE

[75] Inventors: Thomas Moest, Moorrege; Uwe Loeffler, Uetersen; Hans Waiblinger, Bad Oeyhausen, all of Germany

[73] Assignee: Nordmark Arzneimittel GmbH, Uetersen, Germany

[21] Appl. No.: 117,285

[22] Filed: Sep. 7, 1993

[30] Foreign Application Priority Data

Sep. 21, 1992 [DE] Germany .......................... 42 31 493.3

[51] Int. Cl.$^6$ .................. A61K 9/54; B29B 9/08; B29B 9/16
[52] U.S. Cl. ................. 424/458; 424/451; 424/463; 424/468; 424/489; 424/490; 424/493; 424/496; 424/501; 264/4.3; 264/4.4; 264/4.6; 264/117
[58] Field of Search ................ 264/4.1, 4.2, 4.3, 264/4.32, 4.4, 4.6, 4.7, 37, 117; 424/458, 464, 468, 469, 489

[56] References Cited

U.S. PATENT DOCUMENTS

| | | | |
|---|---|---|---|
| 4,205,060 | 5/1980 | Monsimer et al. | 264/4.1 |
| 4,711,782 | 12/1987 | Okada et al. | 264/4.6 |
| 5,160,469 | 11/1992 | Moest | 264/117 |
| 5,292,461 | 3/1994 | Juch et al. | 264/37 |

*Primary Examiner*—Robert A. Dawson
*Assistant Examiner*—Kenneth M. Jones
*Attorney, Agent, or Firm*—Oblon, Spivak, McClelland, Maier & Neustadt

[57] ABSTRACT

A process for producing pellets which are markedly spherical and have a particle size in the range from 0.1 to 4 mm and an apparent density above 0.5 g/cm$^3$, and which are composed of 90–100% by weight of an ephedrine derivative and 0–10% by weight of a pharmaceutical aid, entails suspending ephedrine derivative powder with an average particle size of from 0.5 to 50 μm at 0°–90° C. with stirring in a water-immiscible non solvent with a boiling point in the range from 60° to 160° C., adding 5–60% by weight, based on the ephedrine derivative, of an agglomerating liquid while continuing stirring, and, if there has been previous heating, cooling to from −5 to 25° C. at 5–40K per hour, with the stirring speed being adjusted after the agglomeration of the powder particles to a value which is necessary for the required average particle size, and removing and drying the resulting pellets. A drug which contains the active ingredient in the form of such pellets, with or without slowing of release, is also described.

11 Claims, No Drawings

PRODUCTION OF PELLETS COMPOSED OF AN EPHEDRINE DERIVATIVE

The present invention relates to a simple process for producing pellets which are markedly spherical and are preferably 100% composed of ephedrine derivatives, to the slowing of the release thereof, and to drugs produced therefrom.

Required for building up pellets of ephedrine derivatives by conventional techniques are nonpareils as starter cores for coatings or adhesives and/or other ancillary substances for producing a plastic composition.

These production processes are complicated and they do not allow pellets of ephedrine derivatives with the maximum, i.e. 100%, concentration of active ingredient to be produced; the density of active ingredient is thus limited. However, a high density of active ingredient is necessary, for example, to be able to get relatively large amounts of ephedrine derivatives into hard gelatin capsules of a size which can easily be swallowed.

Ephedrine derivatives in the quality and fineness commercially available, are furthermore prone to aggregation during storage and, in the case of micronized material, to dust formation and are accordingly difficult to handle.

DE 39 29 864 discloses that it is possible to agglomerate the virtually water-insoluble xanthine derivative theophylline to give substantially spherical pellets. Application of the process described in this patent to ephedrine derivatives results, because of the high solubility in water of the ephedrine derivatives, not in pellets but in a two-phase mixture.

It is an object of the present invention to produce in a simple manner spherical pellets of ephedrine derivatives with a high concentration of active ingredient, which simultaneously have a high apparent density of more than 0.5 g/cm$^3$ and low friability and thus, on the one hand, allow a maximum density of active ingredient, e.g. in capsules, and, on the other hand, can be handled optimally.

We have found that this object is achieved by a process for producing pellets which are markedly spherical and have a particle size in the range from 0.1 to 4 mm and an apparent density above 0.5 g/cm$^3$, and which are composed of 90–100% by weight of an ephedrine derivative and 0–10% by weight of a pharmaceutical aid, which comprises suspending ephedrine derivative powder with an average particle size of from 0.5 to 50 μm at 0°–90° C. with stirring in a water-immiscible non solvent with a boiling point in the range from 60° to 160° C., adding 5–60% by weight, based on the ephedrine derivative, of an agglomerating liquid while continuing stirring, and, if there has been previous heating, cooling to from –5° to 25° C. at 5–40 K per hour, with the stirring speed being adjusted after the agglomeration of the powder particles to a value which is necessary for the required average particle size, and removing and drying the resulting pellets.

Examples of ephedrine derivatives for the purpose of the present invention are DL-methylephedrine hydrochloride, pseudoephedrine hydrochloride and pseudoephedrine sulfate.

The starting material is a micronized ephedrine derivative powder with an average particle size in the range from 0.5 to 50, preferably from 1 to 20 μm.

The details of the process are as follows:

The ephedrine derivative powder is dispersed in the liquid while stirring continuously with incipient turbulence, the result being unaffected by whether the powder is added to the liquid or vice versa. Substances which alter the interfacial tension are unnecessary. The liquid is at from 0 to 90° C., preferably from 50 to 65° C. After addition, which can be slowly or quickly, dropwise or all at once, of 5–60, preferably 25–45, % by weight, based on the ephedrine derivative, of the agglomerating liquid which, in the preferred embodiment, comprises a concentrated, in particular (virtually) saturated, aqueous solution of the ephedrine derivative, the temperature is allowed to fall at 5–40 K per hour. Once the initially cloudy dispersion of the powder has become clear owing to agglomeration, the stirring speed is set at that speed which is necessary (as found in preliminary tests) to achieve the required particle size (average pellet size). The average particle size of the pellets can be adjusted in the range from 0.1 to 4 nun, preferably from 0.2 to 3 nun, depending on the amount of agglomerating liquid and the stirrer speed. The particle size distribution is usually narrow within this range, and the particles are uniformly spherical. After cooling to from –5° to +25° C., expediently to room temperature, they are separated from the liquid, washed if necessary with a low-boiling nonsolvent and dried in a conventional way (cf. textbooks of pharmaceutical technology) at 40°–80° C. Their apparent density is more than 0.5 g/cm$^3$. Their friability is very low. In an apparatus for determining the mechanical friability (Born Friabimat SA 400, from Born Gerëtebau, D-3554 Gladenbach), the maximum friability found was only 5% at the very high shaking rate of 990 min$^{-1}$ for 180 sec.

The ratios of the amounts of ephedrine derivative, water-immiscible nonsolvent and aqueous solution are 1 kg: 4–25 l: 0.05–0.6 l.

The process can also be carried out continuously.

A (less preferred) variant of the process is carried out at 0°–40° C. from the outset, and 5–20% by weight, based on the ephedrine derivative, of water are employed as agglomerating liquid, the process being otherwise exactly as described above. In another, even less preferred, variant of the process, a polar organic solvent which, on mixing with the suspending liquid, forms an emulsion which is stable at least until the powder particles have agglomerated-(usually within a few seconds) is employed as agglomerating liquid. Examples thereof are methanol, ethanol, propanol, ethyl acetate, acetone, halohydrocarbons and aromatic hydrocarbons.

The pellets are preferably 100% composed of the active ingredient. However, in principle they can also contain up to 2 or 5 or even 10% by weight of conventional pharmaceutical aids. The latter can be employed in a mixture with the ephedrine derivative powder and be agglomerated together with this, or they are dissolved in the suspending liquid or the agglomerating liquid and adsorbed therefrom onto the powder particles and thus integrated in the agglomerates.

The pellets can be used, directly or after coating to slow release (and/or protect from gastric fluid), to fill hard- gelatin capsules or sachets. Coatings which slow release contain the diffusion-controlling polymers which are insoluble in aqueous medium and are customary for this purpose and are described in textbooks of pharmaceutical technology, e.g. polymethacrylates, cellulose derivatives, vinyl polymers. Owing to the high mechanical strength, the markedly spherical shape and the uniform surface of the pellets, it is possible to obtain a controlled release of active ingredient with very small amounts of coating in a simple way in any suitable coating equipment. Since the pellets are uniformly spherical, closest packing of them in capsules is possible, and thus the capsules have a high content of active ingredient.

Solid drug forms containing the pellets produced according to the invention are hard gelatin capsules, sachets and tablets which have been produced by compression of the pellets using up to 50, preferably up to 10, % by weight, based on the finished tablet, of binders and/or other customary pharmaceutical ancillary substances such as fillers, tablet disintegrants, release-slowing agents, lubricants, colorants.

EXAMPLE 1

506 ml of n-hexane were cooled to 2° C. while stirring in a 1 l jacketed vessel with inclined blade stirrer and baffles. 25 g of micronized pseudoephedrine hydrochloride were added and suspended at a circumferential speed of 3.2 m/s. 7 ml of aqueous pseudoephedrine hydrochloride solution, which was saturated at 2° C., were stirred into the suspension. The circumferential speed was reduced to 1.3 m/s after the agglomeration of the suspended particles, the mixture was slowly cooled at about 10 K/h to −3° C. and then the resulting pellets were removed on a suction funnel and dried in a suitable oven at about 50° C.

The pellets had sizes in the range from 200 µm to 1600 µm with a pronounced maximum at 720 µm.

The apparent density by the DIN 53 468 method was 0.51 g/cm$^3$.

The friability after 180 sec in a Friabimat SA 400 at 990 min$^{-1}$ was less than 3.9%.

EXAMPLE 2

2.5 l of n-hexane were heated to 45° C. while stirring in a 3 l jacketed vessel with inclined blade stirrer and baffles. 0.25 kg of micronized pseudoephedrine hydrochloride was added and suspended at a circumferential speed of 4.4 m/s. 0.1 l of aqueous pseudoephedrine hydrochloride solution, which was saturated at 45° C., was heated to 65° C. and stirred into the suspension. The circumferential speed was reduced to 1.7 m/s after the agglomeration of the suspended particles, the mixture was slowly cooled at about 10 K/h to 20° C. and then the resulting pellets were removed on a suction funnel and dried in a suitable (explosion-proof) oven at about 50° C.

The pellets ranged in size from 300 to 1600 µm with a pronounced maximum at 800 µm.

The apparent density by the DIN 53 468 method was 0.52 g/cm$^3$.

The friability after 180 sec in a Friabimat SA 400 at 990 min$^{-1}$ was less than 1.5%.

EXAMPLE 3

2500 ml of n-hexane were heated to 50° C. while stirring in a 3 l jacketed vessel with inclined blade stirrer and baffles. 0,125 kg of micronized pseudoephedrine sulfate was added and suspended at a circumferential speed of 3.2 m/s. 55 ml of aqueous pseudoephedrine sulfate solution, which was half-saturated at 50° C., were stirred into the suspension. The circumferential speed was reduced to 1.7 m/s after the agglomeration of the suspended particles, the mixture was cooled at about 25 K/h to 20° C. and then the resulting pellets were removed on a suction funnel and dried in a suitable explosion-proof oven at about 50° C.

The pellets ranged in size from 600 to 2000 µm with a pronounced maximum at 1000 µm.

The apparent density by the DIN 53 468 method was 0.54 g/cm$^3$.

The friability after 180 sec in a Friabimat SA 400 at 990 min$^{-1}$ was less than 2.5%.

EXAMPLE 4

500 ml of n-hexane were stirred at room temperature in a 1 l vessel with inclined blade stirrer. 0.1 kg of micronized DL-methylephedrine. HCl was added and suspended at a circumferential speed of 2.6 m/s. 45 ml of aqueous DL-methylephedrine. HCl solution, which was saturated at room temperature, were stirred into the suspension. The circumferential speed was increased to 3.4 m/s after the agglomeration of the suspended particles, the mixture was stirred for 10 minutes and then the resulting pellets were removed on a suction funnel and dried in a suitable oven at about 50° C.

The pellets ranged in size from 100 µm to 4000 µm with a pronounced maximum at 3000 µm, The apparent density by the DIN 53 468 method was 0.56 g/cm$^3$.

The friability after 180 sec in a Friabimat SA 400 at 990 min$^{-1}$ was less than 4.4%.

We claim:

1. A process for producing pellets which are markedly spherical and have a particle size in the range from 0.1 to 4 mm and an apparent density above 0.5 g/cm$^3$, and which are composed of 90–100% by weight of an ephedrine derivative and 0–10% by weight of a pharmaceutical aid, which comprises suspending ephedrine derivative powder with an average particle size of from 0.5 to 50 µm at 0°–90° C. with stirring in a water-immiscible non solvent with a boiling point in the range from 60° to 160° C., adding 5–60% by weight, based on the ephedrine derivative, of a concentrated aqueous solution of the particular ephedrine derivative while continuing stirring, and, if there has been previous heating, cooling to from −5° to 25° C. at 5–40 K per hour, with the stirring speed being adjusted after the agglomeration of the powder particles to a value which is necessary for the required average particle size, and removing and drying the resulting pellets.

2. A process as claimed in claim 1, wherein the ratios of the amounts of ephedrine derivative to water-immiscible suspending liquid to agglomerating liquid are in the range from 1 kg: 4–25 l: 0.5–0.6 l.

3. A process for producing pellets as claimed in claim 1 or 2, wherein the ephedrine derivative employed is DL-methylephedrine hydrochloride, pseudoephedrine hydrochloride or pseudoephedrine sulfate.

4. A process for producing slow release pellets by coating ephedrine derivative pellets which have been produced as claimed in claim 1 or 2 with at least one diffusion-controlling polymer which is insoluble in aqueous medium.

5. A solid drug form for oral administration which contains 50–100% by weight of the ephedrine derivative pellets produced as claimed in claim 1 or 2, or slow release pellets obtained by coating said ephedrine derivative pellets with at least one diffusion-controlling polymer which is insoluble in aqueous medium, or mixtures of the two as active ingredient, with or without conventional pharmaceutical aids.

6. A process for producing slow release pellets by coating ephedrine derivative pellets which have been produced as claimed in claim 3, with at least one diffusion-controlling polymer which is insoluble in aqueous medium.

7. A solid drug form for oral administration which contains 50–100% by weight of the ephedrine derivative pellets produced as claimed in claim 3, or slow release pellets obtained by coating said ephedrine derivative pellets with at least one diffusion-controlling polymer which is insoluble in aqueous medium, or mixtures of the two as active ingredient, with or without conventional pharmaceutical aids.

8. The process of claim 1, wherein said concentrated aqueous solution is a saturated solution.

9. The process of claim 1, wherein 25–45% by weight, based on the ephedrine derivative, of said concentrated aqueous solution is added.

10. The process of claim 1, wherein said pellets are composed of 95–98% by weight of said ephedrine derivative and 2–5% by weight of said pharmaceutical aid.

11. The process of claim 1, wherein said pellets are composed of 100% by weight of said ephedrine derivative.

* * * * *